(12) United States Patent
Sinclair et al.

(10) Patent No.: US 8,202,842 B2
(45) Date of Patent: Jun. 19, 2012

(54) INHIBITION OF CHOLERA TOXINS BY GALATOOLIGOSACCHARIDES (GOS)

(75) Inventors: Haydn Robert Sinclair, Camerton Bath and South East Somerset (GB); Jaap De Slegte, Doetinchem (NL); Gijsbertus Klarenbeek, Ommen (NL)

(73) Assignee: Friesland Brands B.V., Meppel (NL)

( * ) Notice: Subject to any disclaimer, the term of this patent is extended or adjusted under 35 U.S.C. 154(b) by 388 days.

(21) Appl. No.: 12/443,565

(22) PCT Filed: Oct. 1, 2007

(86) PCT No.: PCT/NL2007/050475
§ 371 (c)(1),
(2), (4) Date: Jul. 1, 2009

(87) PCT Pub. No.: WO2008/041843
PCT Pub. Date: Apr. 10, 2008

(65) Prior Publication Data
US 2010/0069322 A1 Mar. 18, 2010

(30) Foreign Application Priority Data
Oct. 2, 2006 (EP) .................................. 06076810

(51) Int. Cl.
*A61K 31/702* (2006.01)
(52) U.S. Cl. .......................................... 514/23; 514/61
(58) Field of Classification Search .................. None
See application file for complete search history.

(56) References Cited

U.S. PATENT DOCUMENTS

| | | | |
|---|---|---|---|
| 6,224,891 B1 | 5/2001 | Rafter et al. | |
| 6,630,452 B2 * | 10/2003 | Wilson | 514/25 |
| 2004/0131659 A1 * | 7/2004 | Gibson et al. | 424/439 |

FOREIGN PATENT DOCUMENTS

| | | |
|---|---|---|
| EP | 0 272 095 A2 | 6/1988 |
| EP | 1 352 967 A1 | 10/2003 |
| WO | 2004/052121 A1 | 6/2004 |
| WO | 2004/089115 A1 | 10/2004 |
| WO | 2005/002766 A1 | 1/2005 |
| WO | 2005/003329 A1 | 1/2005 |
| WO | 2005/035781 A1 | 4/2005 |

OTHER PUBLICATIONS

Fransen, C. et al "alpha-D-Glcp-(1-1)-beta-D-Galp-containing oligosaccharides..." Carbohyd. Res. (1998) vol. 314, pp. 101-114.*
W.H.O. Cholera, 2004, "Weekly Epidemiological Record", Aug. 5, 2005, 80th Year, No. 31, 2005, 80, 261-268.
Mark L. Tamplin, Anne L. Gauzens, Anwarul Huq, David A. Sack and Rita R. Colwell, "Attachment of Vibrio cholerae Serogroup O1 to Zooplankton and Phytoplankton of Bangladesh Waters", Applied and Environmental Microbiology, Jun. 1990, vol. 56, No. 6, p. 1977-1980, © 1990, American Society for Microbiology.
Bukhtiar H. Shah, "Cholera toxin mediated regulation of the expression of Gqα and G11α GTP binding proteins", Experimental and Molecular Medicine, vol. 31, No. 2, 89-94, Jun. 1999.
Shah M. Faruque, M. John Albert, and John J. Mekalanos, "Epidemiology, Genetics, and Ecology of Toxigenic Vibrio cholerae",
Microbiology and Molecular Biology Reviews, Dec. 1998, vol. 62, No. 4, p. 1301-1314, © 1998, American Society for Microbiology.
Teeuwen H. & Bär A., "Defining dietary fibre for nutrition labelling purposes", Intl. Food Ingred., (1/29): 46-49 (1994).
Kurt Wallenfels and OM Prakash Malhotra, "Galactosidases", Adv. Carbohydr. Chem. (1961), 16: p. 239-298.
Keisuke Matsumoto, Youichi Kobayashi, Sadao Ueyama, Tsunekazu Wantanabe, Ryuichiro Tanaka, Tatsuhiko Kan, Akio Kuroda, and Yasuo Sumihara, "Galactooligosaccharides", in Oligosaccharides: production, properties and applications., T. Nakakuki, Editor 1995, Gordon and Breach Science Publishers: Shizuoka, Japan, Chapter 5, p. 90-106.
James L. Leach, Stacey A. Garber, Andrea A. Marcon, and Pedro A. Prieto, "In Vitro and In Vivo Effects of Soluble, Monovalent Globotriose on Bacterial Attachment and Colonization", Antimicrobial Agents and Chemotherapy, Sep. 2005, vol. 49, No. 9, p. 3842-3846.
Tadashi Idota, Hiroshi Kawakami, Yuji Murakami, and Makihiro Sugawara, "Inhibition of Cholera Toxin by Human Milk Fractions and Sialyllactose", Biosci. Biotech. Biochem., 59 (3), 417-419, 1995.
Athanasios K. Goulas, Petros G. Kapasakalidis, Haydn R. Sinclair, Robert A. Rastall, Alistair S. Grandison, "Purification of oligosaccharides by nanofiltration", Journal of Membrane Science, 209(1), 2002, 321-335.
S. Martín-Sosa, M.-J. Martín, L.-A. García-Pardo, and P. Hueso, "Sialyloligosaccharides in Human and Bovine Milk and in Infant Formulas: Variations with the Progression of Lactation" , J. Dairy Sci. 86: 52-59, © American Dairy Science Association, 2003. Gordon J. Leitch, William Burrows and Loren C. Stolle, "Experimental Cholera in the Rabbit Intestinal Loop: Fluid Accumulation and Sodium Pump Inhibition", Journal of Infectious Diseases, 1967, vol. 117(3), p. 197-202.
Jaap De Slegte, et al, "Determination of trans-Galactooligosaccharides in Selected Food Products by Ion-Exchange Chromatography: Collaborative Study", Journal of AOAC International, vol. 85, No. 2, 2002, p. 417-423.
D.J. Harvey, "Quantitative Aspects of the Matrix-assisted Laser Desorption Mass Spectrometry of Complex Oligosaccharides", Rapid Communications in Mass Spectrometry, vol. 7(7), 614-169, 1993.
Fotini N. Lamari, Reinhard Kuhn and Nikos K. Karamanos, "Derivatization of Carbohydrates for chromatographic, electrophoretic and mass spectrometric structure analysis", Journal of Chromatography B, 793(1), 2003, p. 15-36.
R. Dulbecco, M.D. and Marguerite Vogt, M.D., "Plaque Formation and Isolation of Pure Lines with Poliomyelitis Viruses", Published Feb. 1954, from the California Institute of Technology, Pasadena, p. 167-182.
George Tzortizis, Athanasios K. Goulas, Jennifer M. Gee and Glenn R Gibson, "A Novel Galactooligosaccharide Mixture Increases the Bifidobacterial Population Numbers in a Continuous In Vitro Fermentation System and in the Proximal Colonic Contents of Pigs In Vivo", The Journal of Nutrition, 2005, vol. 135, p. 1726-1731, © American Society for Nutritional Sciences.

* cited by examiner

*Primary Examiner* — Leigh Maier
(74) *Attorney, Agent, or Firm* — Hoffman & Baron, LLP

(57) ABSTRACT

The invention relates to nutritional and pharmaceutical compositions comprising non-digestible galactooligosaccharides (GOS) and uses thereof. In particular, it relates to the use of GOS species in preventing or treating disease caused by bacterial toxins. Provided is the use of GOS having a polymerization degree of 5 or higher, preferably 6 or higher, for the manufacture of a nutritional or pharmaceutical composition for the treatment or prevention of an acute or chronic disease associated with or caused by the adhesion and/or uptake of a cholera toxin family member. Also provided is a method for providing a GOS fraction capable of inhibiting cholera toxin (Ctx) binding to GM1 and fractions obtainable thereby.

15 Claims, 6 Drawing Sheets

Figure 1:
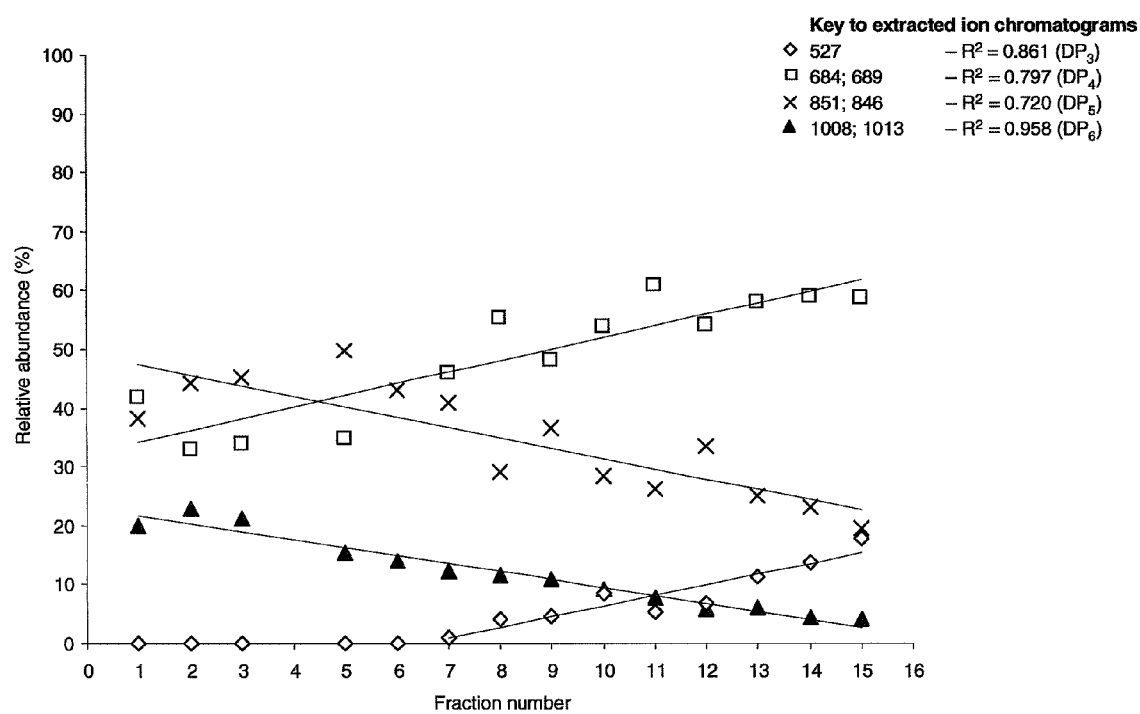

Interval Plot of CT bound vs Dose GOS Fr. 2, Dose CT
Bars represent One Standard Error from the Mean

```
Two-way ANOVA: log CT Bound versus Dose CT, Dose GOS fr. 2

Source          DF      SS        MS         F         P
Dose CT          3   51.1363   17.0454   1439.14   0.000
Dose GOS fr. 2   6    8.0822    1.3470    113.73   0.000
Interaction     18    2.7981    0.1555     13.12   0.000
Error           56    0.6633    0.0118
Total           83   62.6799

S = 0.1088    R-Sq = 98.94%    R-Sq(adj) = 98.43%
```

| LOGEC50 different for each data set | | | |
|---|---|---|---|
| Individual Best-fit values | | | |
| LOGEC50 | 1.473 | 1.501 | 1.482 |
| EC50 | 29.72 | 31.73 | 30.31 |
| 95% Confidence Intervals | | | |
| LOGEC50 | 1.362 to 1.584 | 1.396 to 1.607 | 1.218 to 1.745 |
| EC50 | 23.01 to 38.39 | 24.89 to 40.44 | 16.52 to 55.61 |
| Goodness of Fit | | | |
| Degrees of Freedom | 17 | 17 | 17 |
| $R^2$ | 0.9397 | 0.9414 | 0.8862 |
| Absolute Sum of Squares | 1880 | 1964 | 3071 |
| Sy.x | 10.52 | 10.75 | 13.44 |

One-way ANOVA: % Inhibition versus Fraction

```
Source     DF      SS     MS     F      P
Fraction   14   16825   1202   9.35  0.000
Error      28    3601    129
Total      42   20426
S = 11.34    R-Sq = 82.37%    R-Sq(adj) = 73.56%
```

```
                                Individual 95% CIs For Mean Based on
                                Pooled StDev
Level  N   Mean    StDev    ---+---------+---------+---------+------
  1    3   91.84    1.82                               (-----*----)
  2    3   93.33    2.35                               (----*-----)
  3    3   96.21    1.28                                (----*-----)
  4    3   96.80    0.53                                (-----*----)
  5    3   97.69    0.75                                (----*----)
  6    3   87.04    1.72                           (-----*----)
  7    3   94.00    2.81                               (-----*----)
  8    3   89.05    9.78                            (-----*----)
  9    3   78.66   15.65                      (----*-----)
 10    3   69.90    6.21                 (----*----)
 11    3   56.38   19.82          (-----*----)
 12    3   59.29   18.96           (-----*----)
 13    3   60.94   20.04           (----*-----)
 14    2   32.71   21.85  (-----*------)
 15    2   37.24    3.62    (------*-----)
                         ---+---------+---------+---------+------
                            25        50        75       100
Pooled StDev = 11.34
```

```
One-way ANOVA: % Inhibition versus Fraction

Source     DF      SS      MS      F       P
Fraction   14   22408    1601    9.60   0.000
Error      28    4667     167
Total      42   27075
S = 12.91    R-Sq = 82.76%    R-Sq(adj) = 74.14%

Individual 95% CIs For Mean Based on
                                Pooled StDev
Level   N    Mean    StDev    +---------+---------+---------+---------
  1     3   94.75    5.08                                (-----*----)
  2     3   92.07    3.72                                (----*----)
  3     3   94.94    0.75                                 (----*----)
  4     3   96.60    0.32                                 (----*----)
  5     3   96.53    1.19                                 (----*----)
  6     3   93.54    6.61                                (----*----)
  7     3   93.98    3.21                                (----*----)
  8     3   87.73    9.13                              (----*----)
  9     3   75.98   14.75                         (----*----)
 10     3   66.51    4.42                     (----*----)
 11     3   49.21   21.33             (----*----)
 12     3   56.06   15.79                 (----*----)
 13     3   51.01   32.31              (----*----)
 14     2   18.47   12.63   (-----*-----)
 15     2   40.27   13.37           (------*------)
                             +---------+---------+---------+---------
                             0        30        60        90

Pooled StDev = 12.91
```

INHIBITION OF CHOLERA TOXINS BY GALATOOLIGOSACCHARIDES (GOS)

This application is the U.S. National Phase of, and Applicant claims priority from, International Application Number PCT/NL2007/050475 filed 1 Oct. 2007 and European Patent Application Number EP 06076810.8 filed 2 Oct. 2006 which are incorporated herein by reference.

BACKGROUND OF THE INVENTION

The invention relates to nutritional and pharmaceutical compositions comprising non-digestible galactooligosaccharides (GOS) and uses thereof In particular, it relates to the use of GOS species in preventing, reducing or otherwise treating disease caused by bacterial toxins.

Intestinal infection with *Vibrio cholerae* toxin has afflicted the developing world for almost 200 years. *Vibrio cholerae* is transmitted through the faecal-oral route, most commonly by consumption of contaminated water and to a lesser extent food (W. H. O. Cholera, 2004. Wkly Epidemiol Rec 2005; 80(31):261-8). In immuno-compromised and malnourished individuals, Vibrios survive through the gastric barrier and ultimately colonize the small intestine (Tamplin et al., Appl Environ Microbiol 1990; 56(6):1977-80). Recent cholera outbreaks as a consequence of the Asian Tsunami and Hurricane Katrina in the USA, further illustrates the importance of disease management.

There is however no prophylactic against cholera toxin and without treatment case fatality rates may reach 30-50%. Limited success has been made using two types of Oral Cholera Vaccines (OCV) although they are ineffective against the pathogenic strain *Vibrio cholerae* O139. Furthermore, the discovery that toxin-producing *Vibrio cholerae* strains possess multiple drug resistance has significant implications on the use of antibiotics as a treatment and control strategy. Clearly, there is an urgency to develop alternative technologies to combat cholera and related diseases.

There are many bacterial toxins that bind to ganglioside, an acid glycosphingolipid, as the receptor on the cell surface of target cells and invade target cells by subsequent internalization of the toxin-receptor complex. The best known of these is the cholera toxin (Ctx), an enterotoxin produced by *Vibrio cholerae*, and its specific cell surface receptor was identified as monosialoganglioside gal(beta1-3)galNAc(beta1-4)[sialic acid (alpha2-3)]gal(beta1-4)glc(beta)1-ceramide (GM1).

Cholera toxin is an AB5 hexameric assembly consisting of a ring structure of five identical B-subunits (Ctx-B) and one A-subunit (Ctx-A). As with many other bacterial toxins the catalytic activity resides in Ctx-A, while receptor binding and delivery of the toxin to the target cell is mediated by the Ctx-B pentamer. The binding of B subunits to membrane GM1 is thought to induce a conformational change in the toxin, resulting in the entry of the hexameric assembly comprising the toxic A subunit into the target cell.

The A-subunit displays ADP ribosyltransferase activity towards Gαs, which is a member of the GTP-hydrolyzing protein group, responsible for regulation of many aspects of cell function (Shah B H. Exp Mol Med 1999; 31(2):89-94). Gαs regulates the activity of adenylate cyclase and determines the concentration of cGMP in the host cell. The A subunit then ADP ribosylates the alpha subunit of Gs, knocking out the innate GTPase activity. Consequently the stimulus cannot be switched off and so adenylate cyclase continues producing cAMP, keeping the cascade turned on. Normally, in the absence of Ctx, an on-off mechanism ensures that the Gαs is activated as required by the cell in response to stimulation of intestinal adenylate cyclase. This system normally therefore maintains the cGMP concentration high enough to perform its function (Faruque et al., Mol Biol Rev 1998; 62(4):1301-14). Uncontrolled ADP-ribosylation of Gαs results in a continual increase in adenylate cyclase activity that ultimately causes high levels of cGMP to accumulate. In the gut cGMP levels affect sodium and chloride transporters, causing ion imbalance and disruption in membrane osmotic potential. The resultant massive efflux of chloride and bicarbonate ions into the small intestinal lumen pulls large quantities of water with it by passive osmosis.

The class of AB5 toxins may be subdivided into families based on sequence homology and receptor tropism. Both cholera toxin and the *E. coli* heat-labile enterotoxins LT and LT-II are structurally related. The B-subunits of both toxins have high affinity for the oligosaccharide portion of a number of glycolipids including GM1. The adherence of either cholera toxin or the heat-labile enterotoxin of *Escherichia coli* to GM1 present on the surface of epithelial cells lining the intestine is the first step of a series that results in the induction of watery diarrhoea. While cholera is more severe, both can lead to death as a result of severe dehydration.

DESCRIPTION OF THE INVENTION

It is an aim of the present invention to provide compositions that are effective in the prophylactic and/or therapeutic treatment of diseases associated with pathogenic bacterial toxins of *Vibrio cholerae* and Enterotoxigenic *E. coli*. In particular, the present inventors set out to identify compounds that are of use as inhibitors of adhesion of cholera toxin to its receptor GM1 with the underlying idea that targeting the bacterial toxin can circumvent drug resistance of the bacterial strain.

Surprisingly, it was found that certain fractions of a non-digestible, food-grade oligosaccharide preparation are highly efficient inhibitors of Ctx-B binding to its natural receptor. More specifically, fractions enriched in galacto-oligosaccharides (GOS) with a polymerization degree of five or higher, comprising GOS pentasaccharides (herein also referred to as DP5) and GOS hexasaccharides (DP6), were found to be effective anti-Ctx-B adhesives by preventing Ctx binding to GM1 on a target cell.

The invention therefore relates to a composition comprising galacto-oligosaccharides (GOS), wherein GOS species having a polymerization degree of 5 or higher, preferably 6 or higher, are present in an amount of more than 30% by weight (w %), based on the total dry weight of all GOS species present in the composition. Also provided is the use of GOS having a polymerization degree of 5 or higher, preferably 6, for the manufacture of a nutritional or pharmaceutical composition for the treatment or prevention of an acute or chronic disease associated with or caused by the adhesion and/or uptake of a cholera toxin family member.

In another aspect, the invention provides a fractionation method for the isolation of a GOS fraction having Ctx-inhibitory activity from a GOS mixture. Also provided is a GOS fraction obtainable by said method and the use of said fraction as anti-Ctx-B-adhesive.

Also provided is a composition, for example a pharmaceutical or nutritional composition or a concentrate thereof, comprising a high amount of GOS DP5 and/or DP6 species.

GOS belong to the group of non-digestible carbohydrates that may be regarded as soluble dietary fibres, because they fit the generally accepted definition of dietary fibre including both biochemical and nutritional/physiological criteria (Food Industry ad hoc Working Group on Dietary Fibre (1994) Int.

Food Ingred., 1, 46-49). GOS have received increasing interest, because they can promote the proliferation of bifidobacteria and lactic acid bacteria in the human intestine and thus enhance the human health. GOS are not only characterized as prebiotics that improve intestinal health but were also shown to reduce colon cancer risk. The possible antitumor activity of GOS might be accounted for by the possible antitumor action of butyrate, one of the substances produced from GOS in the colon.

GOS can be produced enzymatically using the purified D-lactose fraction of whey as a substrate (Wallenfels et al., Adv Carbohydr Chem, (1961). 16: p. 239-98). The β-galactosidase enzyme from *Aspergillus oryzae* has a transgalactosyl catalytic activity on lactose resulting in the formation of di- to octasaccharides composed of 1-7 galactose units linked to a glucose molecule at the reducing end, i.e. (galactose)$_n$ glucose, where n is 1-7 (Matsumoto et al., Galactooligosaccharides., in Oligosaccharides: production, properties and applications., T. Nakakuki, Editor. 1995, Gordon and Breach Science Publishers: Shizuoka, Japan. p. 90-106). However, enzymatic synthesis produces GOS mixtures that are frequently impure. For example, the commercial syrup Vivinal GOS® contains only 59% GOS w.w$^{-1}$, with lactose, glucose and galactose accounting for the remaining 41%. Among the GOS species present in VivinalGOS, disaccharides (DP2) and trisaccharides (DP3) are most abundant, representing approximately 33 w % and 39 w %, respectively, based on the total dry weight of all GOS species. DP4 and DP5 represent about 18 w % and 7 w %. GOS species having a polymerization degree of six and higher represent only about 3 w % of the GOS species in VivinalGOS. Other commercially available GOS mixtures are similarly enriched in lower molecular weight GOS species, in particular in GOS di- and trisaccharides. As disclosed herein below, the present inventors developed a method for the fractionation of the complex mixture of GOS species derived from whey. Following removal of glucose and galactose, the mixture was separated by ion exchange chromatography. This resulted in 15 fractions with a different GOS species profile, i.e. differing in the relative abundance of GOS tri-, tetra-, penta-, and hexasaccharides, herein referred to as DP3, DP4, DP5 and DP6, respectively. With increasing fraction number, DP5 and DP6 abundance was shown to decrease in a stepwise manner with a simultaneous increase in DP3 and DP4, indicating a shift from predominantly DP6-DP5 containing fractions to DP4-DP3 containing fractions.

Competitive ELISA-tests were performed wherein the GOS fractions were evaluated for their ability to inhibit binding of the Ctx B-subunit to GM1. This revealed that GOS fractions relatively enriched in GOS pentasaacharides (DP5) and hexasaccharides (DP6) and having a low relative abundance of DP3 and DP4 are particularly potent inhibitors of Ctx adhesion. The term 'relatively enriched' is meant to indicate that the abundance is increased as compared to the unfractionated starting material.

Active GOS fractions included those comprising 15 w % or more of DP6 based on the total dry weight of GOS species present in the fraction, corresponding to at least 15 mg/ml in the ELISA test. Furthermore, DP5 was present in the active fractions in an amount of at least 40 w % based on all GOS species present, corresponding to at least 40 mg/ml in the test. Without wishing to be bound by theory, statistical correlations between the inhibition constant of each fraction and the composition of each fraction determined using mass spectrometry data suggests that DP6 is the most likely inhibitory component of fractionated VivinalGOS. However, other GOS species present in the active fractions may account for some or all of the observed activity as well.

Therefore, the invention provides in one aspect the use of GOS DP5-6 (or possibly an even higher degree of polymerization) for the manufacture of a nutritional or pharmaceutical composition for the treatment or prevention of an acute or chronic disease associated with or caused by the adhesion and/or uptake of a cholera toxin family member. The nutritional or pharmaceutical composition is suitable for the prevention or treatment of acute or chronic disease caused by a cholera toxin family member, in particular diarrhoeal diseases. In one embodiment, the disease is caused by *V. cholerae* cholera toxin (Ctx-B) or heat-labile enterotoxin (LT-B) of enterotoxigenic *E. coli* (ETEC).

A further aspect of the invention relates to an anti-adhesive composition comprising galacto-oligosaccharides (GOS), wherein GOS species having a polymerization degree of 5 or higher, preferably 6 or higher, are present in an amount of more than 30% by weight (w %), preferably at least 35 w %, more preferably at least 40 w %, based on the total dry weight of all GOS species present in the composition. In one embodiment, the composition comprises GOS having a polymerization degree of 6 in an amount of at least 10% by weight (w %), preferably at least 15 w %, more preferably at least 20 w %, based on the total dry weight of all GOS species present in the composition. Alternatively or additionally, a composition comprises GOS having a polymerization degree of 5 in an amount of at least 15% by weight (w %), preferably at least 20 w %, more preferably at least 30 w %, based on the total dry weight of all GOS species present in the composition.

A specific aspect relates to a composition comprising from about 10 w % to about 20 w % GOS DP6, from about 40 w % to about 50 w % DP5, the remainder being GOS DP4.

A composition according to the invention may comprise other components in addition to the GOS species, for example a diluent, carrier and/or compounds of nutritional and/or pharmaceutical value. A composition can also be a concentrated GOS composition, for example wherein all GOS species present in the composition make up at least 50 w %, preferably at least 60 w %, more preferably at least 70 w %, such as 80 w %, 85 w %, 90 w %, 95 w % or even 99 w %, based on the dry weight of the composition. Furthermore, the above relative percentages DP5 and DP6 in a composition can increase up to high values. Compositions consisting essentially solely of GOS DP5 and/or DP6 are also envisaged. Thus, compositions are provided wherein the GOS species present consist of only GOS DP5, only GOS DP6 or a mixture of GOS DP5 and DP6.

The above data illustrate that fractionation itself has increased Ctx-binding inhibitory efficacy by concentrating particular GOS species, i.e. GOS penta- and hexasaccharides, that are otherwise diluted in the commercial GOS formulation. The process thus provides a rapid and effective means of removing low molecular weight carbohydrates that have no prebiotic, nutraceutical and/or biological properties. The concentration of active carbohydrates, in particular GOS DP5 and/or DP6, allows to prepare a composition that has a higher (Ctx anti-adhesive) activity per unit (dry) weight. Such a composition is advantageously used in the manufacture of pharmaceutical or nutraceutical formulations for the treatment or prevention of an acute or chronic disease associated with or caused by the adhesion and/or uptake of a cholera toxin family member.

Dose-response studies to determine the EC50 of DP6-riched GOS fractions revealed EC50 values for DP6 ranging from between 30 to 42 mg/ml. EC50 refers to the concentration of inhibitor that competes for half the specific binding and is the same as the IC50 value. Correlating the EC50 values to the relative DP6 content suggests an EC50 value of about 5 mg/ml for DP6.

Accordingly, in one embodiment the anti-adhesive composition comprises at least 0.5% (w/w), preferably at least 0.7%, more preferably at least 1.0% GOS hexasaccharides. For example, said composition is a liquid composition comprising at least 5 mg/ml GOS hexasaccharides, preferably at least 7 mg/ml, more preferably at least 10 mg/ml The use of various types of oligosaccharides as inhibitors of pathogen adhesion to mammalian cells has been previously described. For example, Leach et al. (Antimicrob Agents Chemother. 2005 September; 49(9): 3842-3846) disclosed the ability of a soluble, monovalent globotriose to interfere with attachment and colonization of uropathogenic *Escherichia coli*.

WO 2005/02766 discloses the use of several oligosaccharides as inhibitor of pathogen adhesion to mammalian cells. Compounds tested included commercially obtained GOS (VivinalGOS; vGOS) and pectic oligosaccharides that had been purified by ultrafiltration to remove nitrates. No GOS fractionation was performed. vGOS tested positive in the inhibition of adhesion of one strain of *E. coli* VTEC (O157:H7). Neither *V. cholera*, nor its toxins, are mentioned in WO 2005/02766.

U.S. Pat. No. 6,224,891 describes the use of a multivalent derivative of α-galactose oligosaccharides comprising the αGal(1→4)βGal subunit as an inhibitor of shiga liketoxins (SLT) binding to cells that express GB3 (neutral glycolipid, globotriaosylceramide Gb3 (α-D-Gal(1→4)β-D-Gal(1→4) β-D-Glc(1→O-ceramide) also known as CD77) at their cell surface. SLT is produced by pathogenic *E. coli*. STARFISH is the name given to a specific synthetic oligovalent inhibitor developed to block the binding of SLT. It is a synthetic molecule built with pseudo five-fold symmetry. The core is a functionalized glucose molecule into which are grafted spacers and at the tips of the spacers are placed 2 identical trisaccharides that correspond to the oligosaccharide recognized by Shiga like toxin. The oligosaccharide structures of U.S. Pat. No. 6,224,891 are unrelated to GOS hexasaccharides and are ineffective as anti-Ctx adhesives. This is not surprising considering the structural difference between the SLT receptor (ganglioside Gb3) and the Ctx-receptor (ganglioside GM1).

Compositions comprising a mixture of GOS species, including penta- and hexasaccharide GOS structures, are known in the art.

WO2005/003329 discloses a mixture of 20-35% w/v of disaccharides, 20-35% w/v of trisaccharides, 15-25% w/v of tetrasaccharides and 10-20% w/v of pentasaccharides, and the use thereof for the preparation of a medicament for preventing the adhesion of pathogens or toxins to the gut wall.

WO2004/052121 relates to nutritional compositions comprising GOS and FOS oligosaccharides for controlling inflammatory bowel disease and related disorders. Exemplary compositions comprise GOS having 2 to 6 saccharide units. A preference is indicated for compositions comprising 0-30% of weight pentasaccharides, more preferably 2-10%, even more preferably 7% by weight. A similar preference is expressed in WO2004/089115 and WO2005/035781.

Tzortzis et al. (2005, The Journal of Nutrition, Vol. 135, pages 1726-1731) evaluated the prebiotic potential of a GOS mixture comprising 9.9% disaccharides, 23.1% trisaccharides, 11.55% tetrasaccharides and 10.45% pentasaccharides, based on the total dry weight of the powder composition. The mixture strongly inhibited the adhesion of some bacteria in an in vitro gut model system. This effect was attributed to the disaccharide fraction.

Clearly, a composition according to the invention wherein GOS species having a polymerization degree of 5 or higher, preferably 6 or higher, are present in an amount of more than 30% by weight (w %) is not disclosed or suggested in the art. The strong inhibitory effect of DP5 and/or DP6 on uptake or binding of a cholera toxin family member as disclosed herein can neither be derived from the prior art.

The only disclosure of an oligosaccharide having effect on cholera toxin action is by Idota et al. (Biotech. Biochem, 59 (3), 417-419 (1995) wherein 3-sialyllactose, present in significant amounts in human milk, is identified as an inhibitor of fluid accumulation induced by cholera toxin in rabbit intestines.

Taken together, the present finding that the high molecular weight GOS species are capable of inhibiting cholera toxin binding is not disclosed or suggested in the prior art.

As will be clear from the above, a preferable composition has a relatively high abundance of GOS penta- and/or hexasaccharides. In one embodiment, the invention provides a composition that is enriched for GOS hexasaccharides. The expression "enriched for" is meant to indicate that the composition has been treated or processed by any means with the specific aim to increase the concentration of the desired GOS species. This can be through overall concentration of a composition and/or through the removal of structures other than the desired GOS penta- and/or hexasaccharides. For example, based on the total amount of individual GOS structures (e.g. GOS species with a distinct degree of polymerization) present in the composition, the composition comprises at least 7, preferably at least 10, more preferably at least 15 (w/w) % of GOS having a polymerization degree of six. In one embodiment, GOS DP5-6 represent from about 15 up to about 100% by weight of the total GOS structures, for example 20%-100%, 25%-90%, 35%-95%, 40%-60%, 50%-75%, 25-100%, 35-100%, 40-100%, 50-100%, 60-100%, 75-100%.

A composition preferably has a relatively low abundance of GOS trisaccharides. For example, among the total amount of individual GOS structures present in the composition, the composition comprises less than 10, preferably less than 7, more preferably less than 5 (w/w) % of GOS with a polymerization degree of three. In one embodiment, a GOS composition is essentially free of GOS trisaccharides.

The relative abundance of GOS tetrasaccharides in a GOS composition provided herein is may be less than 50, preferably less than 45, more preferably less than 40 (w/w) %.

In a further aspect, the composition is essentially free of mono- and/or di-saccharides, in particular galactose and/or lactose. Lactose can be hydrolyzed to form glucose and galactose using β-galactosidase. These monosaccharides can be removed using cation exchange chromatography.

In a preferred embodiment, a composition of the present invention comprises beta-linked galactosyl residues with a polymerization degree of six, in particular GOS hexasaccharides with β(1-4) and/or β(1-6) linkages. Beta-linked GOS hexasaccharides can for example be obtained from a GOS mixture that is produced enzymatically from whey lactose as a substrate using bacterial β-galactosidase. For example, β-galalactosidase from *Aspergillus oryzae* has a transgalactosyl catalytic activity on lactose resulting in the formation of a GOS mixture comprising di- to octasaccharides composed of 1-7 beta-linked galactosyl units. Such a mixture is also known in the field as "transgalacto-oligosaccharides", abbreviated to TGOS or TOS.

Commercial GOS preparations can be used advantageously to produce a composition of the invention. A particularly suitable source of GOS DP5 and/or DP6 for practising the present invention is the commercially available prebiotic ingredient containing galacto-oligosaccharides marketed under the tradename VivinalGOS® from Friesland Foods Domo®, The Netherlands.

Individual GOS structures can be separated and isolated from a mixture of GOS species by methods known in the art. For example, nanofiltration can be used as described in Goulas, A. K., et al. (Journal of membrane science, 2002. 209(1): p. 321). In a preferred embodiment, a GOS mixture is fractionated using cation exchange chromatography. More preferably, the counter ion of the cation exchange resin is potassium ($K^+$). As exemplified herein, the cation ion exchange resin marketed under the tradename UniBead UBK-530 (Mitsubishi Chemical Industries Ltd, Tokyo, Japan) is particularly suitable for the fractionation of a GOS mixture having no anti-Ctx adhesive activity into fractions having anti-Ctx adhesive activity.

The degree of polymerization in each of the fractions can be determined using various analytical techniques known in the art, such as high-performance anion-exchange chromatography with pulsed amperometric detection (HPAEC-PAD) or Matrix-assisted laser-desorption ionization—time of flight (MALDI-TOF) mass spectrometry or used in combination.

In a further aspect, the invention provides a method for providing a GOS fraction having anti-Ctx adhesive activity comprising the steps of:
- providing a mixture of galacto-oligosaccharides (GOS) with varying degrees of polymerization;
- (optionally) removing free lactose by converting the free lactose of the GOS mixture into monosaccharides (glucose and galactose);
- applying said (lactose free) GOS mixture to a cation exchange resin;
- step-wise eluting GOS species having an increasing degree of polymerization using a water mobile phase and collecting separate eluent fractions each comprising GOS species with a distinct degree of polymerization;
- analyzing each eluent fraction for the inhibitory effect on Ctx binding to GM1; and
- selecting one or more fraction(s) capable of inhibiting Ctx binding to GM1.

The cation exchange resin is preferably Unibead UBK-530 or a functional equivalent thereof, more preferably in the potassium form.

EP1352967 reports on a method for preparing GOS by mixing galactose with a galactosidase, resulting in the formation of GOS, using a cation exchange resin to separate the mixture in three different fractions. However, in contrast to the method of the present invention, it does not involve the stepwise elution/fractionation of a GOS mixture into individual fractions containing GOS species having an increasing degree of polymerization. Rather, the method of EP1352967 is aimed at separating and concentrating GOS, from lactose, and all GOS species elute in the second fraction.

According to the invention, the inhibitory effect on Ctx binding is readily determined using methods known in the art, for example GM1-competitive-Enzyme Linked Immuno Sorbent Assay (GM1-ELISA) using Ctx coupled to horseradish peroxidase (Ctx-HRP). Preferably, the selected fraction(s) is/are capable of inhibiting at least 50%, more preferably at least 70%, most preferably at least 80%, like 90-99%, of the binding of Ctx to GM1 observed in the absence of said fraction(s).

Also provided is an anti-adhesive GOS fraction obtainable by the method described above. Optionally, the GOS fraction obtained may be concentrated and/or purified further, for example to increase the concentration of anti-Ctx adhesive GOS structures, such as GOS hexasaccharides. For example, baker's yeast may be used for this purpose The step of providing a mixture of galacto-oligosaccharides (GOS) with varying degrees of polymerization for instance comprises subjecting whey permeate or lactose to enzymatic transgalactosidation using β-galactosidase.

Alternatively, said mixture of galacto-oligosaccharides (GOS) with varying degrees of polymerization comprises a commercial GOS mixture, for example the GOS syrup marketed under the trade name Vivinal GOS.

A composition of the invention can exist of or comprise a GOS fraction with anti-Ctx adhesive properties obtainable by the method described above.

A composition of the invention may furthermore comprise other beneficial components, including non-digestible oligosaccharides other than GOS. It has been shown that food-grade non-digestible sialylated oligosaccharides (SOS) are capable of inhibiting cholera toxin binding to its receptor. In one embodiment, the invention provides a composition comprising GOS penta- and/or hexasaccharides, furthermore comprising food-grade SOS. (non-digestable sialylated oligosaccharides)-SOS can be isolated from natural sources, e.g. from egg-yolk or dairy product. The commercially available sialyl-oligosaccharide mixture Sunsial E® from hen egg yolk can be used which contains about 17% SOS and about 68% protein.

In one embodiment, the composition comprises SOS derived from milk, in particular bovine milk. Five sialyligosaccharides were identified in bovine milk, of which 6'-sialyllactosamine and 3'-sialyllactose were the most abundant (S. Martín-Sosa et al, (2003). J. Dairy Sci. 86:52-59).

It is noted that the structures of SOS are significantly different from the GOS species identified herein as being active anti-Ctx adhesives.

Also provided is the use of GOS penta- and/or hexasaccharides, or of a GOS fraction obtainable by the method described herein above for the manufacture of a nutritional or pharmaceutical composition for the prevention or treatment of acute or chronic disease caused by cholera toxin (Ctx) and/or heat-labile enterotoxin, in particular diarrhoeal diseases.

Also provided is the use of GOS penta- and/or hexasaccharides, or of a GOS fraction obtainable by the method described herein above, for the in vitro inhibition of binding of the cholera toxin family member, in particular the pentameric B-subunit thereof, to its receptor GM1.

The medicament, nutritional or pharmaceutical composition of the invention may optionally comprise pharmaceutical acceptable carriers. Further, according to the invention there is provided a combined pharmaceutical preparation for simultaneous, separate or sequential use for inhibiting pathogen adhesion to mammalian cells, e. g. for controlling, e. g. treating, preventing or ameliorating acute or chronic bacteria-associated enteric disorders in a mammal that are dependent on GM1-mediated uptake of bacterial toxins.

The compositions of the invention optionally comprise conventional food additives, such as any of emulsifiers, stabilizers, sweeteners, flavourings, colouring agents, preservatives, cheating agents, osmotic agents, buffers or agents for pH adjustment, acidulants, thickeners, texturisers, and so on.

Pharmaceutical compositions and dietary supplements may be provided in the form of soft gel, sachets, powders, syrups, liquid suspensions, emulsions and solutions in con venient dosage forms. In soft capsules the active ingredients are preferably dissolved or suspended in suitable liquids, such as fatty oils, paraffin oil or liquid polyethylene glycols. Optionally stabilisers may be added.

The amount of GOS penta-/hexasaccharide or active GOS fraction incorporated into the compositions of the invention may depend on the form of the compositions of the invention, e. g. a powder or a composition ready-for-consumption. Accordingly, suitable amounts of GOS penta- and/or hexasaccharide or active GOS fraction comprised in compositions according to the invention are in the range of up to about 2-100% by weight, for example from about 5 to about 95% by weight, e. g. from about 15 to about 90% by weight, based on the total weight of the composition.

The amount and dosage regimen of the compositions of the invention to be administered is determined in the light of various relevant factors including the purpose and manner of administration, the age, sex, body weight and overall health and condition of individual subject and the severity of the subject's symptoms. When the composition according to the invention is supplied in the form of a food or beverage, a suitable serving size of GOS hexasaccharide may be from about 1 mg to about 20 g, preferably from about 10 mg to about 10 g, more preferably from about 10 mg to about 1 g. If provided in a pharmaceutical form, suitable daily doses of the anti-Ctx adhesive GOS of the invention are up to about 250 mg, preferably up to about 150 mg, more preferably up to about 100 mg, and optimally in the range of about 1 mg to about 100 mg.

Pharmaceutical or dietary supplement forms may be made by conventional compounding procedures known in the pharmaceutical art, that is, by mixing the active substances together with edible pharmaceutically acceptable solid or liquid carriers and/or excipients, e. g. fillers such as cellulose, lactose, sucrose, mannitol, sorbitol, and calcium phosphates and binders, such as starch, gelatin, tragacanth, methylcellulose and/or polyvinylpyrrolidone (PVP). Optional additives include lubricants and flow conditioners, e. g. silicic acid, silicon dioxide, talc, stearic acid, magnesium/calcium stearates, polyethylene glycol (PEG) diluents, disintegrating agents, e. g. starch, carboxymethyl starch, cross-linked PVP, agar, alginic acid and alginates, colouring agents, flavouring agents, and melting agents. Dyes or pigments 'may be added to the tablets or dragee coatings, for example for identification purposes or to indicate different doses of active ingredient.

Optionally, the compositions according to the invention may be nutritionally complete, i. e. may include vitamins, minerals, trace elements as well as nitrogen, carbohydrate and fatty acid sources so that they may be used as the sole source of nutrition supplying essentially all the required daily amounts of vitamins, minerals, carbohydrates, fatty acids, proteins and the like. Accordingly, the compositions of the invention may be provided in the form of a nutritionally balanced complete meal, e.g. suited for oral or tube feeding. Alternatively, the compositions of the invention may be provided as part of a meal, i. e. a nutritional supplement, e.g. in the form of a health drink. It may be desirable to provide the composition of the invention in the form of a low calorie meal replacement or other nutritional product. In this case the meal replacement or other nutritional product is preferably low fat, i.e. less than about 10% fat or substantially fat-free, i. e. less than about 2.5% contributed by fat, such as about 2% fat, based on the total caloric content of the composition. Suitably, a single serving of a low calorie meal replacement will have a caloric value of less than about 1000 cal, and preferably between about 200 cal and about 500 cal.

Suitable compositions of the invention, e.g. suitable low calorie nutritional product, may include soft drink, such as juice, smoothie or soy-based drink, or dispersed in foods of any sort, such as, dairy bars, soups, breakfast cereals, muesli, candies, tabs, cookies, biscuits, spreads, infant formula, pre-infant formula, weaning food, confectionery, cakes, crackers, such as a rice crackers, and dairy products, such as milkshake, yoghurt drink, fermented milk.

The compositions of the invention optionally comprise conventional food additives, such as any of emulsifiers, stabilizers, sweeteners, flavourings, colouring agents, preservatives, chelating agents, osmotic agents, buffers or agents for pH adjustment, acidulants, thickeners, texturisers, and so on.

In a further aspect of the invention, there is provided a use of a GOS fraction or a composition of the invention as food additive.

Suitable product formats according to the present invention include solution, ready-for-consumption composition, e. g. ready-to-drink compositions, instant drink, liquid comestibles, like soft drinks, juice, sports drinks, milk drinks, milkshakes, yogurt drinks or soup. In a further embodiment of the invention, the compositions of the present invention may be manufactured and sold in the form of a concentrate, a powder, or granules, e. g. effervescent granules, which are diluted with water or other liquid, such as milk or fruit juice, to yield a ready-for-consumption composition, e.g. ready-to-drink compositions or instant drink.

The composition of the invention may be in any form suitable for human administration, and in particular for administration in any part of the gastrointestinal tract. Enteral administration of the compositions of the invention, and preferably oral administration, and administration through a tube or catheter, are covered by the present invention.

The compositions of the invention may be administered under the supervision of a medical specialist, or may be self-administered.

A pharmaceutical or nutritional composition or a food or beverage incorporating GOS penta-/hexasaccharide according to the invention can be safely consumed by anyone. They are especially recommended for anyone perceived to be at risk from diseases, conditions and symptoms related to toxins of the cholera toxin family, for example immuno-compromised and/or malnourished individuals.

In one embodiment of the invention, the invention pertains to a method of treating and/or preventing a disease associated with or caused by the uptake of a cholera toxin family member, e.g. Ctx or LT, in a mammal, including human, in need of such a treatment, comprising administering to said mammal an effective amount of GOS Penta-/hexasaccharide or active GOS fraction according to the invention. As used herein, the term "an effective amount" refers to an amount effective to achieve a desired therapeutic effect, such as treating and/or preventing acute symptoms associated with toxin action, in particular fluid accumulation in the intestines.

In another embodiment of the invention, there is provided a method for inhibiting cholera toxin adhesion to mammalian cells, e.g. to gut or intestinal epithelial mammalian cells.

In a further embodiment, the present invention relates to a process for the production of the compositions of the invention, wherein such process comprises intimately admixing the components of the composition of the invention with pharmaceutically or nutritionally acceptable excipients. Such processes are well known to one skilled in the art.

The utility of all the compositions of the present invention may be observed in standard clinical tests in, for example, indications as described hereinabove, for example using one or more anti-Ctx adhesive GOS fractions of the invention, in a range of from about 1 g to 15 g, e.g. about 10 g, for a mammal, and in standard animal models. The relief in symptoms characterizing acute or chronic cholera toxin-associated enteric disorders provided by the compositions may be observed in standard animal tests for example using the experimental cholera model in the rabbit intestinal loop (Leitch et al., J Infect Dis. 1967 June; 117(3): 197-202).

LEGENDS TO THE FIGURES

FIG. 1: Correlation between the cation exchange purified GOS fraction number and relative abundance of GOS tri-, tetra-, penta- and hexa-saccharides (indicated as $DP_3$, $DP_4$, $DP_5$ and $DP_6$, respectively). For experimental details see Example 1.

Figure 2:
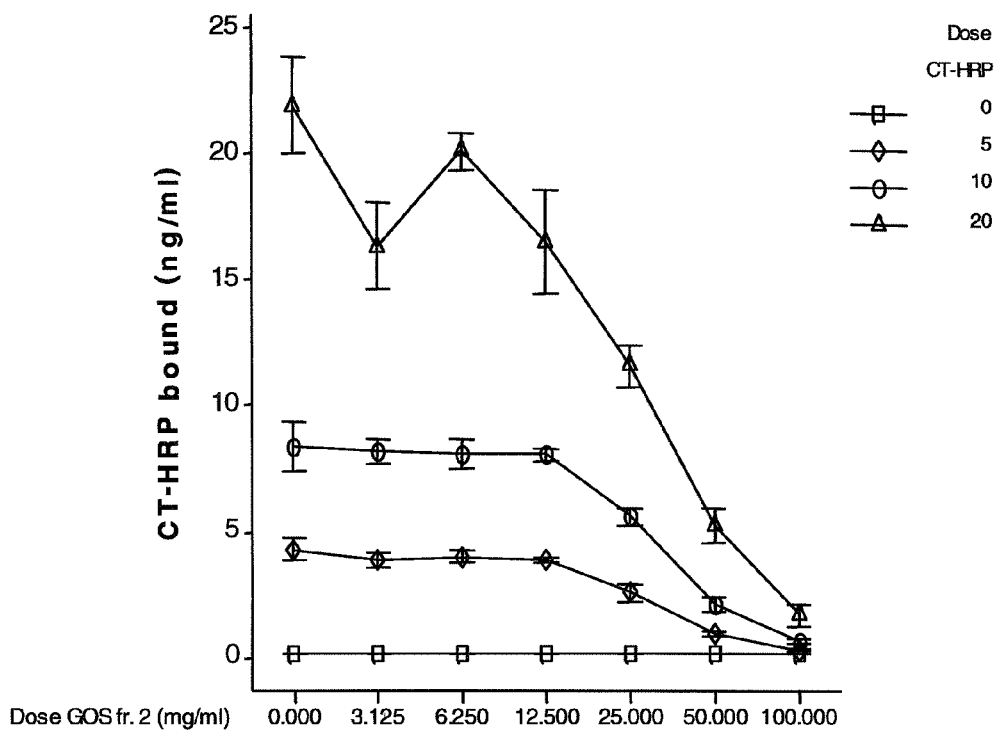

FIG. 2: GOS fraction 2 inhibition of Ctx-HRP n=6. P=0.000 indicates that the interaction between GOS fraction 2 and Ctx-HRP in this GM1-linked ELISA is highly significant. ANOVA calculated from log transformed Ctx-HRP bound values. For experimental details see Example 2.

Figure 3:
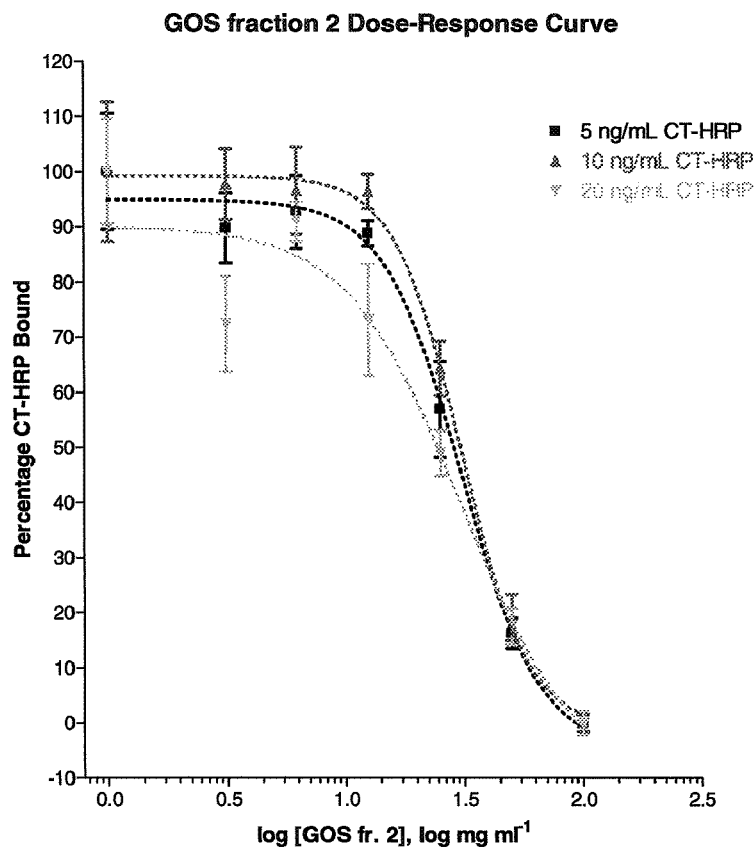

FIG. 3: GOS fraction 2 dose response. n=6. Global $r^2$=0.925 indicates a strongly fitted sigmoidal response. Differences between log EC50 and EC 50 values were found not to be significantly different (P=0.9411) therefore the null hypothesis was not rejected.

FIG. 4: Inhibitory activity of GOS fractions 1-15 on Ctx-HRP binding to GM1. See FIG. 1 for GOS species content of each fraction. Panel A: 100 mg ml−1 versus inhibition of 10 ng ml−1 Ctx-HRP. n=6. The large $r^2$ value indicates that 73.56% of the variation is caused by differences in the species composition between the GOS fraction. Panel B: 100 mg ml−1 GOS fractions 1-15 versus inhibition of 20 ng ml−1 Ctx-HRP. n=6. The large $r^2$ value indicates that 74.14% of the variation is caused by differences in the species composition between the GOS fractions.

Figure 5:
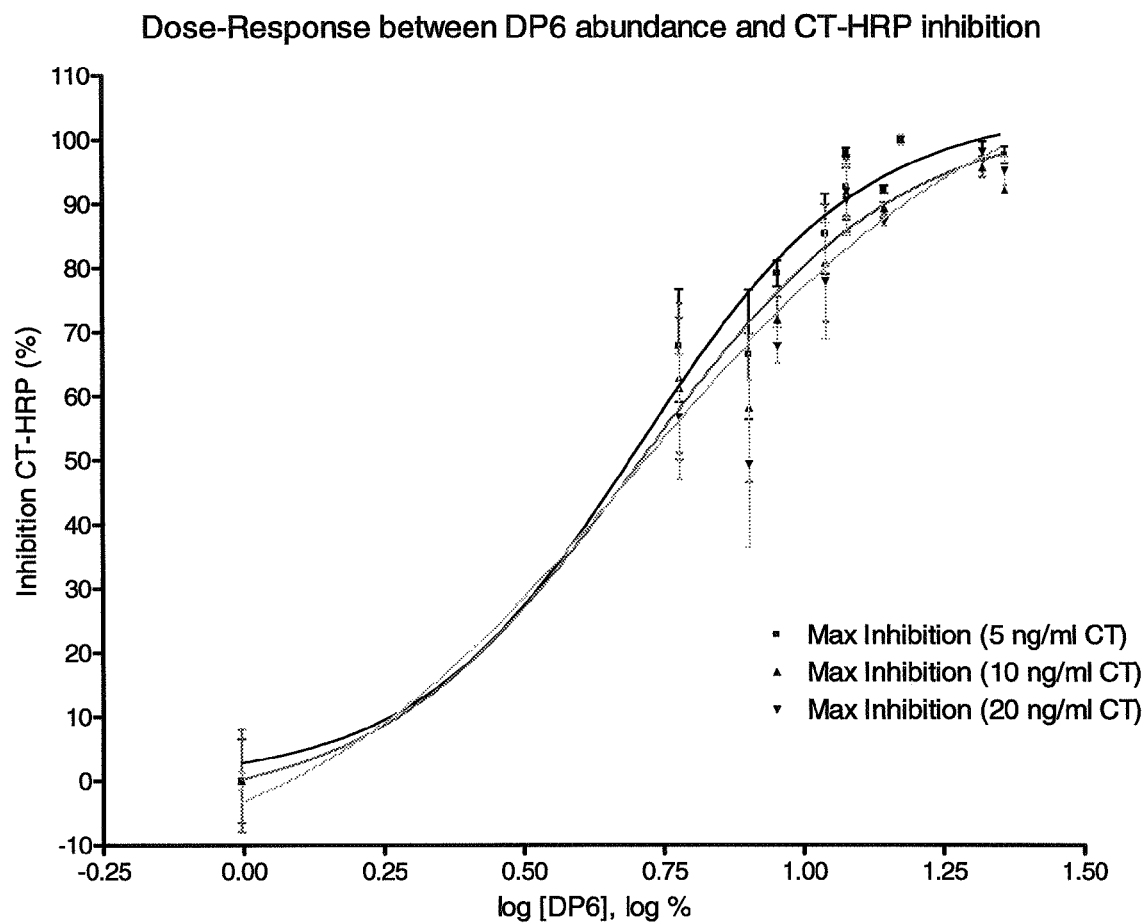

FIG. 5; Correlation between the dose of DP6 and inhibition of Ctx-HRP n=6. P=0.2748 indicates that there is no statistical difference between each of the fitted sigmoidal dose-response curves. Furthermore the concentrations of Ctx-HRP does not affect the efficacy of DP6. DP6 values were transformed to log scale. $R^2$=0.8516 and EC50=5.10% DP6

EXAMPLES

Example 1

Purification and Characterisation of 'Food-Grade' galacto-oligosaccharides (GOS) using Cation Exchange Chromatography and HILIC-ESI-MS Enzymatically produced galactooligosaccharides derived from whey, consist of di- to heptasaccharides composed of 1-7 galactose units linked to a glucose molecule at the reducing end. This complex GOS mixture is an example of a commercial product containing non-digestible health promoting oligosaccharides and low molecular weight sugars, which merely increase the calorific value of the product. This example describes the use of cation-exchange resin in the sodium form to chromatographically remove glucose and galactose on a semi-preparative scale. Resultant oligosaccharide fractions were successfully characterized and profiled using hydrophilic interaction chromatography (HILIC) coupled to electrospray mass spectrometry (ESI-MS).

1. Materials and Methods 1.1. Chemicals

All solutions were prepared using ultrapure MilliQ water. The commercial galactooligosaccharide mixture Vivinal-GOS® used had a typical composition of: 73% w.w$^{-1}$ dry matter of which 57% w.w$^{-1}$ was galacto-oligosaccharides; 23% w.w$^{-1}$ lactose anhydrous; 19% w.w$^{-1}$ glucose anhydrous and 0.9% w.w$^{-1}$ galactose (Friesland Foods Domo, Zwolle, The Netherlands). Standards for HPLC stand curve generation were analytical grade D-(+)-Glucose monohydrate and β-Lactose, purchased from Sigma-Aldrich Company Ltd. (Gillingham, Dorset, UK). HPLC grade MeOH and $H_2O$ were purchased from Rathburns Chemical Co., (Peebleshire, Scotland), $NH_4AC$ from BDH (VWR International, Poole, UK). Maltoheptanose, maltohexanose, maltopentanose, maltotetraose, raffinose, lactose and glucose were purchased from Sigma-Aldrich (Gillingham, Dorset, UK). Fractionated GOS powders were produced with UBK-530 cation-exchange resin (Mitsubishi chemical corporation, Tokyo, Japan). 2-AB (2-aminobenzamide) labelled Glucose Homopolymer (GHP) ladder was purchased from Ludger Ltd (Abingdon, Oxfordshire, UK). Initially all oligosaccharides were dissolved in $H_2O$ to 10 mg m$^{-1}$, and then further diluted before injection.

1.2. Lactose Hydrolysis of VivinalGOS® with β-galactosidase;

Removal of Lactose from VivinalGOS was performed to improve the separation between glucose and galactose and trisaccharides—heptasaccharides. In the reaction lactose is hydrolysed to form glucose and galactose. These monosaccharides are retained with higher affinity in cation exchange. To this end, VivinalGOS® was pre-treated with the β-galactosidase preparation Maxilact® L5000 before cation exchange purification. Initially 30% solution w.w$^{-1}$ of VivinalGOS® was prepared and adjusted to pH 6.5 using 1 M sodium hydroxide. After heating to 40° C., 0.9 g of Maxilact was added to the VivinalGOS® and incubated for 4 hours. After treatment the solution was pH adjusted to 4.5 and heated to deactivate the lactase for 10 minutes at 100° C. Precipitated enzyme was removed by centrifugation at 19,000 RPM for 60 minutes. The resultant lactose free VivinalGOS solution was used in cation exchange experiments.

1.3. Preparative Scale Cation Exchange Chromatography Purification of VivinalGOS®

The technique is adapted from Matsumoto et al. (*Method for producing galactooligosaccharides*, E.P. Office, Editor. 1987). Briefly, Na-form resin Unibead UBK-530 was selected (Mitsubishi Chemical Industries Ltd, Tokyo, Japan). 2000 ml of UBK-530 resin was hydrated and fines removed according to the manufacturers instructions. Afterwards, the resin was treated with 1 M KCl solution for 12 hours in a stirring water bath at 20° C. in order to exchange the Na$^+$ ion with a K$^+$ ion.

The column was composed of borosilicate glass with an internal diameter of 0.05 m and length 1 m. This glass column was surrounded by an acrylic plastic thermostat jacket (Pharmacia XK-50/100 column, Amersham Pharmacia Biotech, Buckinghamshire, UK). Additional Teflon tubing was wrapped around the column to act as a heat exchanger. The column was heated with a Haake Model FE circulating water bath (Haake, UK). Samples were pumped through the resin using a pulsation free 3-piston pump module (Model C-601, Buchi, Flawil, Switzerland). Separated carbohydrates from the columns were detected using a differential refractometer, Gilson model 132 RI detector (Anachem, Bedfordshire, UK), which was purged with eluent at the start of each experiment.

Prior to sample loading all equipment including ion-exchange resin, column, VivinalGOS® and water used for elution were heated to 55° C. over a 60 minute period to ensure equilibrium. In total 1800 ml of the 2000 ml UBK-530 resin was loaded into the column. Initially demineralised water was pumped through at 1 ml min$^{-1}$ gradually increasing to a final flow of 15 ml min$^{-1}$ in order to avoid pressure shock to the resin. All eluent was degassed using helium before use. Following pre-treatment with Maxilact L5000, 150 ml of 30% w.w$^{-1}$ lactose free VivinalGOS® solution was injected onto the column at 15 ml min$^{-1}$. Concentrations higher than this produced disorder in the separation pattern. The void volume of this column was 675 ml or 45 minutes before the carbohydrate began to elute. Eluent containing separated carbohydrates were collected every minute in fractions until no further carbohydrate was detected by the RI detector (Model 2128 Fraction Collector, Bio-Rad, Hertfordshire, UK).

1.4. High-Performance Anion-Exchange Chromatography Determination of the Vivinal GOS Purity using Preparative-Scale Cation Exchange Chromatography Fractions collected during ion exchange chromatography were analysed using high-performance anion-exchange chromatography with pulsed amperometric detection (HPAEC-PAD) (Dionex corp., Calif., USA) following the protocol developed for galactooligosaccharides by de Slegte et al. ("Determination of trans-Galactooligosaccharides in Selected Food Products by Ion Exchange Chromatography: Collaborative Study". Journal of AOAC International, 2002. 85 Part 2: p. 417-423). Briefly, a CarboPac PA-1 pellicular anion-exchange resin column with 250×4 mm internal diameter guard column of sulfonated ethylvinylbenzene-divinylbenzene particles was used. The mobile phase was a gradient of (A) 12.5 mM NaOH, (B) 125 mM NaOH, and (C) 125 mM NaOH with 500 mM sodium acetate. The eluent gradient for the analysis was performed as previously reported by de Slegte et al. 20 μL of each sample was injected and analyzed at room temperature with a flow rate of 1 ml min$^{-1}$.

1.5. Hydrophilic Interaction Chromatography (HILIC)

ZIC®-HILIC, PEEK Column, 150×2.1 mm 5 μm was selected because stationary phase 'bleed' from the column has been shown to be particular low (SeQuant A B, Umea, Sweden). The zwitterionic ZIC®-HILIC stationary phase is attached to porous silica. The separation is achieved by a hydrophilic partitioning mechanism superimposed on weak electrostatic interactions. The other analysis parameters were: 1 μL injection volume, 214 nm UV detection, and 31 min runtime. One of the GOS fractions was analysed at 20, 30, 40, 50 and 60° C. All further chromatographic runs were at 60° C. Methanol was used rather than acetonitrile because it was possible to dissolve the GOS fractions in higher concentrations of MeOH:H$_2$O than ACN:H$_2$O. Injecting carbohydrates in 100% H$_2$O did not allow the solvent to partition into the stationary phase and consequentially the sample eluted as a 'plug' without separation. The mobile phase was composed of 95% MeOH-5 mM NH$_4$AC in H$_2$O. Gradient experiments varied the time in which a 50:50 MeOH:H$_2$O concentration by programming the gradient pumps. The low water content of 5% was used to maintain suitable hydration and improve electrostatic interactions between stationary and mobile phase. The Agilent 1100 HPLC system consisted of an Agilent 1100 series capillary pump with an online degasser (Agilent, Stockport, UK) a UV detector, autosampler, and Dionex CS 14 cation-exchange guard (4 mm×50 mm). Flow rates varied from 100 to 200 μl min$^{-1}$ and 214 nm was monitored with the UV detector.

1.6. Electrospray Ionization Mass Spectrometry to Analyze Sugars

The description of the ionization and detection including specific operating parameters are described according to modified manufacturers instructions (Bruker Daltonics microTOF instrument, Bruker Daltonics, Bremen, Germany).

2. Results 2.1. Cation Exchange Fractionated GOS

The cation exchange method was modified from Matsumoto et al. [12] following personal communications with J. de Slegte at Royal Friesland Foods. Previously, counter ions Na$^+$, K$^+$ and Ca$^{2+}$ were tested to determine which gave the cleanest separation of GOS from lactose, galactose and glucose. The potassium form of the UBK-530 resin gave best results with regard to Vivinal GOS® separation and was therefore chosen for further experiments (unpublished data). HPAEC-PAD was used on each 1-minute fraction to determine the oligosaccharide composition. Initial fractions contained high concentrations of GOS. There was a shift in composition from high molecular weight galactooligosaccharides to glucose and galactose with each successive fraction collected from the IEX column. UBK-530 resin displayed excellent resistance to compression, sugars were also eluted without organic solvent and he column did not require equilibration between injections, therefore, semi continuous purification was achieved.

2.2. Analysis and Comparison between GOS Fraction Numbers 1-15

Using a column heated to 60° C.±0.5° C., a flow rate of 200 μl min$^{-1}$ and gradient of 95% MeOH-5 mM NH$_4$AC in water to 50% MeOH-5 mM NH$_4$AC in water in 25 minutes partially resolved the composition of GOS fractions 1-15. Using the software integration features in DataAnalysis v3.2 software, it was possible to integrate the area under each of the groups of sugars identified as DP$_3$ followed by DP$_4$, DP$_5$, DP$_6$ and DP$_7$.

By integrating the extracted ion chromatograms of each sugar it was possible to calculate an abundance value for the di-, tri-, tetra-, penta-, hexa- and hepta-saccharides in each fraction. However, it has been shown that oligosaccharides do not ionise with the same efficiency in the source (Harvey, D. J., Rapid communications in mass spectrometry: RCM, 1993. 7(7): p. 614) and so expressing data in the form of relative abundance is common practice in mass spectrometry (Lamari, et al., J Chromatogr B Analyt Technol Biomed Life Sci, 2003. 793(1): p. 15-36). If individual sugars fail to ionize with equal efficiency or rather hexasaccharides (DP6) ionize poorly, relative ionization abundance in percentage reduces this effect when making comparisons between fractions. For example if the total abundance of all carbohydrate adducts in fraction X is added and percentages calculated for each DP, individual DP (all DP3 for instance) abundance is plotted relative to all ions formed. FIG. 1 is a graphical plot of the relative abundance of tri-, tetra-, penta- and hexa-saccharides against fraction number. Linear regression between fraction number and DP$_6$ abundance gives a correlation coefficient of 0.958, indicating there is a strong relationship between these 2 variables. The probability of obtaining a calculated r value of greater than 0.9 with greater than 10 replicates when 2 variables are unrelated is <0.001. The DP5 abundance is also inversely related to fraction number with a coefficient of 0.720.

Example 2

Inhibition by galactooligosaccharides on Binding of Cholera Toxin to its Receptor In this Example the ability of galactooligosaccharide fractions obtained in Example 1 to inhibit cholera toxin binding to GM1 is measured using competitive ELISA. The bioactivity or EC50 values are to be correlated with structural information from the HILIC-ESI-MS experiments of Example 1 to elucidate which structures from GOS are the most efficient at inhibiting the binding of Ctx to GM1 natural receptors. The natural receptor GM1 was used as a model sugar since it has been shown to have most efficacy for cholera toxin.

1. Materials and Methods 1.1 Chemicals

Analytical grade D-(+)-Glucose monohydrate, β-Lactose, monosialoganglioside-GM1 isolated from bovine brain, TWEEN® 20, Bovine serum albumin (BSA), 3,3',5,5'-Tetramethylbenzidine (TMB), dimethyl sulfoxide (DMSO) and sulphuric acid ($H_2SO_4$) were all purchased from Sigma Aldrich (Gillingham, Dorset, UK). Phosphate buffered saline (PBS) was purchased from Oxoid Ltd (Basingstoke, Hamps, UK) in tablet form and corresponded to the original formulation of Dulbecco and Vogt (1954) except that calcium and magnesium are omitted. Each tablet was diluted in distilled water following the manufacturer's instructions. *Vibrio cholera* toxin B-subunit conjugated to horseradish peroxidase was imported by and purchased from Quadratech Ltd, Surrey, UK (manufactured by List Biologicals, Calif., USA). Galactooligosaccharides were a gift from Friesland Foods Domo (Zwolle, The Netherlands) and purified and fractionated using cation exchange chromatography prior to use. All solutions were prepared using ultrapure MilliQ water.

1.2 Inhibitory GM1-Linked ELISA

Microtiter plates (F96 Maxisorp; Fisher Scientific, Loughborough, UK) were incubated at room temperature overnight with 100 μl of 500 ng $ml^{-1}$ ganglioside GM1 dissolved per well in phosphate-buffered saline (pH 7.2) containing 160 mM NaCl and 9 mM potassium phosphate (PBS). Unattached ganglioside was removed by washing the wells three times with PBS containing 0.1% Tween 20. Additional binding sites on the plate surface were blocked by incubating the wells with 200 μl of a 2% (w/v) bovine serum albumin (BSA)-PBS solution overnight at room temperature and then washed with 0.1% Tween 20-PBS three times.

Test solutions were prepared in 0.1% BSA-PBS; each consisting of 5, 10 and 15 ng/mL of Ctx-B5 horseradish peroxidase conjugate, pre-incubated with potential inhibitors for 2 h at room temperature. After the addition of 200 μL of each test solution, plates were incubated for 2 hours at room temperature. Unbound toxin was removed by washing three times with 0.1% Tween 20-PBS. The following steps then revealed toxin bound to GM1: (1) incubation with 100 μl of freshly made (TMB) solution (1 mg of TMB in 500 μl DMSO, 50 ml of 0.1 M potassium citrate buffer and 5 μl of 30% hydrogen peroxide) for 15 min at room temperature. TMB is a noncarcinogenic substitute for benzidine and was used as peroxidase substrate. The substrate produced a soluble end product that was pale blue in colour and read spectrophotometrically (Genios, Tecan UK Ltd, Thatcham, UK) after stopping with 2 M $H_2SO_4$ (resulting in a yellow colour) at 450 nm.

All experiments were carried out in quadruplicate and validated against a standard curve of 0, 0.97, 1.95, 3.90, 7.81, 15.62, 31.25 and 62.5 ng $ml^{-1}$ toxin peroxidase conjugate. A stock solution of 30 ng $ml^{-1}$ Ctx-HRP was prepared and used throughout every plate as a control to measure the intra assay coefficient of variation or absorbance drift and assay stability. Unknown absorbance readings and subsequent EC50 values were calculated from the standard curve and compared with Prism version 4.0 software (GraphPad® Software Inc, Calif., USA). ANOVA was calculated using Minitab® version 14 (Mintab Ltd, Coventry, UK).

The statistical mean of each set of absorbance readings was used to calculate the concentration of cholera that was not inhibited and consequently able to bind to the immobilized GM1 surface. Higher absorbance readings were indicative of greater concentrations of uninhibited cholera and/or poor inhibitor performance. Error bars reflect the standard error of the mean of the actual uninhibited Ctx-HRP on the different days of the replicate experiments.

2. Results 2.1 Inhibition by GOS Fractions of Ctx-HRP Binding to GM1-ELISA

FIG. 2 shows an interaction plot between the concentration of Ctx-HRP bound and dose of GOS fraction number 2 at each different concentration of Ctx-HRP. GOS fraction number 2 was chosen as an example, although similar levels of inhibition were typically observed for fractions 1-9 with a visual reduction in colorimetric response at all 3 concentrations of Ctx-HRP with at least 12.5 mg $ml^{-1}$ sugar. The larger error bars at low concentrations of GOS are caused by partial inhibition between replicates and/or weak affinity at low concentrations. Furthermore, two-way ANOVA between the concentration of Ctx-HRP bound and dose GOS fraction 2 and dose Ctx-HRP confirms that the GOS dose affects the inhibition (P<0.001). In addition, the descriptive statistic $R^2$ ($\eta^2$ or eta squared) represents the fraction of the overall variance attributable to differences amongst 'dose Ctx-HRP' and 'dose GOS' means. $R^2$ of 98.43% means that a large fraction of the variation is due to the treatment that defines a group (i.e., increasing concentration) and further strengthens the relationship between Ctx-HRP bound and GOS fraction 2 concentrations. A large F value means that the variation between 'dose GOS' and 'Ctx-HRP bound' mean values is more than would be observed by chance, further supporting the concept that 'dose GOS' affects Ctx-HRP bound.

The mean concentrations of Ctx-HRP bound in all GOS fraction 2 experiments without any inhibitor were 4.25, 8.31 and 21.90 ng $ml^{-1}$ and not 5, 10 and 20 ng $ml^{-1}$ as calculated. However, these variations are within the limits of the intra and inter assay coefficients (not shown). Moreover, there were also minor differences in the zero inhibitor values between fractions, therefore in order to make comparisons between fractions the EC50 value was calculated and compared between curves. Prism® v4 software (GraphPad Software, Inc, Calif., USA) was used to transform Ctx-HRP concentration from ng $ml^{-1}$ to percentage inhibition and normalise inhibitor values onto a log scale. Prism® fitted a sigmoidal dose-response curve or three-parameter logistic (FIG. 3). Normalizing in this way extends the y-axis vertically from 0 to 100% by definition; therefore the accuracy of the minimum and maximum values was essential. Prism also compared the dose-response curves at each concentration of Ctx-HRP and found that the EC50 values were not statistically different (P=0.9411, F, 0.061). This indicates that GOS fraction 2 effectively inhibited Ctx-HRP with equal efficacy, irrespective of the amount of Ctx-HRP as shown in FIG. 3. This situation is likely to change if the concentration of Ctx-HRP was increased above 20 ng $ml^{-1}$. Conversely, this assay is constrained by the linearity of the peroxidase substrate standard curve and the observation that half maximal binding is estimated to be 15 ng $ml^{-1}$ or 0.153 nM [34]. The EC50 was calculated as 30.77 mg $ml^{-1}$, with a closely fitted sigmoidal curve with $R^2$ of 0.9253.

Figure 4A:
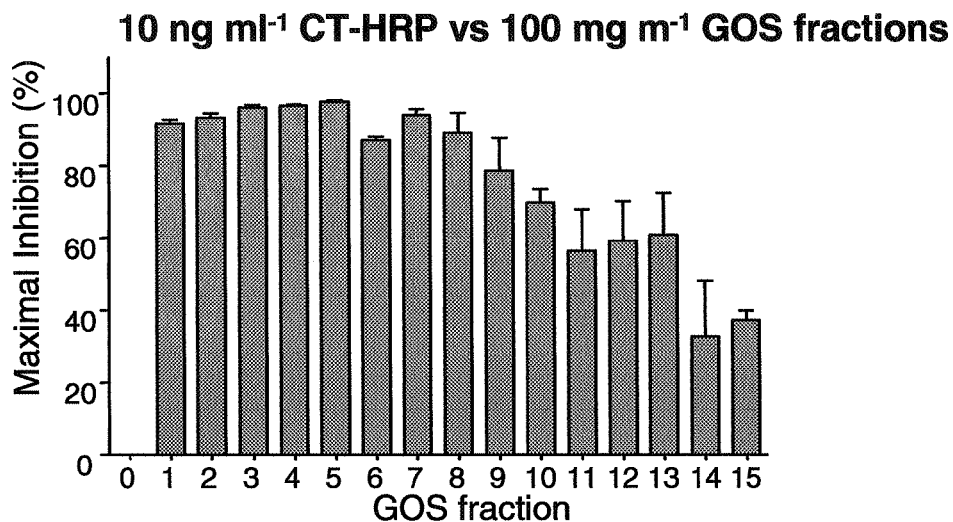

Between fractions 1-10, the EC50 value varied minimally, in particular compare the EC50 values of 30.77 mg $ml^{-1}$ GOS fraction 2 and 42.19 mg $ml^{-1}$ GOS fraction 8. Ctx-HRP EC50 values could not be obtained for fractions 9-15 because either total inhibition was not observed or the sigmoidal dose-response curve fitted poorly. Therefore, in order to compare efficacy between fractions, the maximal inhibition with 100 mg ml$^{-1}$ GOS fraction was chosen. Interestingly GOS fraction numbers 11-15 produced plots with larger standard error bars, however, this is likely to be caused by non-specific binding or weaker affinity for Ctx-HRP. Despite this observation, one-way ANOVA analysis between 10 ng ml$^{-1}$ (0.102 nM) Ctx-HRP inhibition and each GOS fraction reveals there is a statistical difference between fractions with P<0.0001 (FIG. 4A). Fractions 1-8 inhibit between 91.84% and 89.05% Ctx-HRP, respectively. Comparing this percentage inhibition to the actual concentration of Ctx-HRP bound when incubated with 100 mg ml$^{-1}$ GOS fr. 2, the value is low (0.621 ng ml$^{-1}$) with 95% confidence limits 0.374-0.868 ng ml$^{-1}$. Furthermore, at 100 mg ml$^{-1}$ there is 95% certainty that IEX fraction 2 will inhibit between 95.67% and 89.95% of the Ctx-HRP, 95% of the time.

Figure 4B:
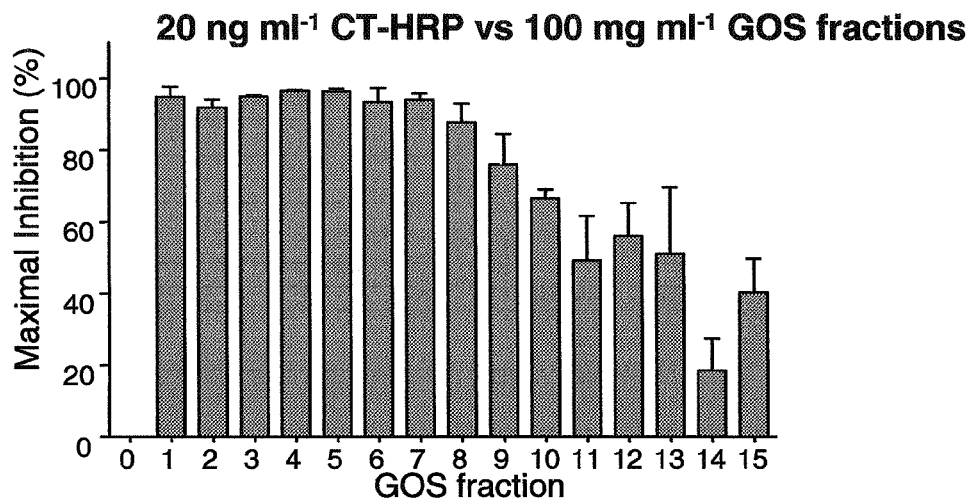

FIG. 4B similarly compares 20 ng ml$^{-1}$ (0.204 nM) Ctx-HRP inhibition and each GOS fraction at 100 mg ml$^{-1}$. The inhibitory values were again expressed relative to Ctx-HRP bound with 0 mg ml$^{-1}$ inhibitor. GOS fractions 1-7 provide a minimum of 92% inhibition, whereas fractions 10-15 inhibit less than 66% Ctx-HRP with higher standard deviation between replicates. As before, one-way ANOVA analysis between 20 ng ml$^{-1}$ Ctx-HRP inhibition and each GOS fraction reveals there is a statistical difference between fractions with P<0.0001. The maximum difference in inhibition between different concentrations of Ctx-HRP is small in comparison to the affect observed between GOS fractions. Using cation exchange chromatography, a difference between the GOS species profile of each fraction was elucidated. HILIC-ESI-MS measured directly the differences between degrees of polymerisation in each fraction and showed that $DP_6$ and $DP_5$ concentrations decrease with successive fraction number, whereas $DP_3$ and $DP_4$ concentrations increase. Using mathematical models and statistical techniques, the correlation between changes in mass and biological efficacy was investigated.

2.2 Comparison between Inhibition of Ctx-HRP by GOS Fractions and GOS Composition FIG. 1 shows the change in GOS profile between each fraction separated using cation exchange chromatography as described in Example 1. Since the abundance of $DP_6$ seemed to correlate closely with Ctx anti-adhesive activity, the mean of bound Ctx-HRP was plotted against relative abundance of GOS $DP_6$ (hexasaccharides) in each fraction (FIG. 5). The correlation followed an exponential decay relationship; moreover, expressing the $DP_6$ concentration in log scale (semi-log plot) results in a sigmoidal scattergram. Prism software was then used to normalise the data in terms of inhibition Ctx-HRP and fit sigmoidal dose-response curve to calculate EC50 values for each concentration of Ctx-HRP. As before, EC50 refers to the concentration of inhibitor that competes for half the specific binding and is the same as the $IC_{50}$ value. The 95% confidence interval for each curves EC50 value overlaps and furthermore, there is no difference between log EC50 values statistically. The EC50 values were calculated to be 4.40, 5.11 and 6.25% $DP_6$ relative abundance, with a global calculated figure of 5.1%. This similarity further confirmed that the efficacy of GOS is similar across the Ctx-HRP concentrations used. Importantly, the biological activity of each GOS fraction was measured at a concentration of 100 mg ml$^{-1}$ and therefore the main difference between each fraction is the relative sugar abundance and thus composition.

3. Conclusion

GOS fractions 1-8 display consistently high levels of inhibition against cholera toxin in the ELISA assay. The GOS species profiles of each GOS fraction from HILIC-ESI-MS were correlated against the concentration of bound Ctx in ELISA and revealed DP6 structures as the most likely inhibitory ligand with global $R^2$ value of 0.925. Example 1 herein above shows that DP6 abundance decreases in a stepwise manner with each fraction from 23% in GOS fraction 1 to 9% in GOS fraction 10 and 0% in GOS fraction 16. Also, DP5 abundance seems to correlate with inhibitory activity. A simultaneous increase in $DP_3$ and $DP_4$ was observed, indicative of a shift from predominantly $DP_6$-$DP_4$ containing fractions to $DP_4$-$DP_3$ containing fractions. High overall GOS fraction concentrations may be important in order to maintain a $DP_6$ concentration high enough to fully inhibit Ctx-HRP. This might explain why un-fractionated GOS does not inhibit Ctx whatsoever (GOS fraction 0; FIGS. 4A and B). Therefore, fractionation itself has increased efficacy by concentrating particular GOS species, i.e. GOS penta- and hexasaccharides that are otherwise diluted in the commercial GOS formulation.

The invention claimed is:

1. A composition comprising galacto-oligosaccharides (GOS), wherein GOS species having a polymerization degree of 5 or higher are present in an amount of at least 35% by weight (w %), based on the total dry weight of all GOS species present in the composition, and food grade non-digestible sialylated oligo-saccharides (SOS).

2. Composition according to claim 1, comprising GOS species comprising β-linked galactosyl residues.

3. Composition according to claim 1, wherein all GOS species present in the composition make up at least 50 w % based on the dry weight of the composition.

4. Composition according to claim 1, comprising GOS having a polymerization degree of 5 in amount of at least 40 w % based on the dry weight of the composition.

5. Composition according to claim 1, comprising GOS having a polymerization degree of 6 or higher in amount of at least 10 w %, based on the dry weight of the composition.

6. Composition comprising galacto-oligosaccharides (GOS), wherein the ratio between GOS species having a polymerization degree of 5 or more are present in excess over GOS species having a polymerization degree of less than 5, based on the dry weight of said GOS species in the composition.

7. Composition according to claim 1, wherein said composition is essentially free of mono- and/or disaccharides, in particular galactose and/or glucose and/or lactose.

8. Composition according to claim 1, comprising at least 15 w % of GOS species having a polymerization degree of 6 based on the total dry weight of all GOS species present in the composition.

9. The composition of claim 1 wherein the GOS species has a polymerization degree of 6 or higher.

10. The composition of claim 1 wherein the GOS species comprises β(1-4) and / or β(1-6) linkages.

11. The composition of claim 1 wherein all GOS species present in the composition make up at least 60 w % based on the dry weight of the composition.

12. The composition of claim 1 wherein all GOS species present in the composition make up at least 70 w % based on the dry weight of the composition.

13. The composition of claim 1 wherein the SOS is derived from milk.

14. The composition of claim 1 wherein the SOS is 3'-sialyllactose.

15. The composition of claim 13 wherein the milk is bovine milk.

* * * * *